(12) United States Patent
Maliga et al.

(10) Patent No.: US 7,176,355 B2
(45) Date of Patent: Feb. 13, 2007

(54) PLASTID RRNA OPERON PROMOTER ELEMENTS FOR CONSTRUCTION OF CHIMERIC PROMOTERS FOR TRANSGENE EXPRESSION

(75) Inventors: Pal Maliga, East Brunswick, NJ (US); Jon Y. Suzuki, Hilo, HI (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 65 days.

(21) Appl. No.: 10/737,251

(22) Filed: Dec. 15, 2003

(65) Prior Publication Data

US 2004/0221338 A1 Nov. 4, 2004

Related U.S. Application Data

(60) Provisional application No. 60/433,302, filed on Dec. 13, 2002.

(51) Int. Cl.
C12N 15/82 (2006.01)
C12N 15/11 (2006.01)
A01H 5/00 (2006.01)

(52) U.S. Cl. .................. 800/298; 435/320.1; 536/24.1

(58) Field of Classification Search ..................... None
See application file for complete search history.

(56) References Cited

U.S. PATENT DOCUMENTS

| | | | |
|---|---|---|---|
| 5,451,513 A | 9/1995 | Maliga | |
| 5,545,818 A | 8/1996 | McBride | |
| 5,877,402 A * | 3/1999 | Maliga et al. | ............... 800/298 |
| 6,297,054 B1 | 10/2001 | Maliga | |
| 6,376,744 B1 | 4/2002 | Maliga | |
| 6,388,168 B1 | 5/2002 | Maliga | |
| 6,472,586 B1 | 10/2002 | Maliga | |
| 6,624,296 B1 | 9/2003 | Maliga | |
| 6,987,215 B1 | 1/2006 | Maliga | |

OTHER PUBLICATIONS

Tozawa, Y., et al., "Nuclear encoding of a plastid sigma factor in rice and its tissue- and light-dependent expression," Nuc. Acids Res., 26:415-419, (1998).
Tan, S., et al., "Characterization of two cholorplast RNA polymerase sigma factors from Zea mays: photoregulation . . . ," Proc. Natl. Acad. Sci. USA, 96:5316-5321, (1999).
Svab, Z., et al., "High-frequency plastid transformation in tobacco by selection for a chimeric aadA gene," Proc. Natl. Acad. Sci. USA, 90:913-917, (1993).
Sun, E., et al., "In vitro analysis of the pea chloroplast 16S rRNA gene promoter," Mol. and Cell. Biol., 9:5650-5659, (1989).
Strittmatter, G., et al., "Identification of an rRNA operon promoter from Zea mays chloroplasts which excludes the proximal . . . ," EMBO J., 4:599-604, (1985).
Staub, J.M., et al., "Accumulation of D1 polypeptide in tobacco plastids is regulated via the untranslated region . . . ," EMBO J., 12:601-606, (1993).

Sriraman, P., et al., "The phage-type PclpP-53 plastid promoter comprises sequences downstream of the transcription initiation site," Nuc. Acids Res., 26:4874-4879, (1998).
Sriraman, P., et al., "Transcription from heterologous rRNA operon promoters in chloroplasts reveals requirement for specific . . . ," Plant Physiol., 117:1495-1499, (1998).
Shiina, T., et al., "rbcL transcript levels in tobacco plastids are independent of light: reduced dark transcription rate is . . . ," Plant Cell, 10:1713-1722, (1998).
Ross, W., et al., "E. coli Fis protein activates ribosomal RNA transcription in vitro and in vivo," EMBO J., 9:3733-3742, (1990).
Orozco, E.M., et al., "An in vitro system for accurate transcription initiation of chloroplast protein genes," Nuc. Acids Res., 13:1283-1302, (1985).
Liere, K., et al., "In vitro characterization of the tobacco rpoB promoter reveals a core sequence motif conserved between phage-type plastid . . .," EMBO J., 18:249-257, (1999).
Lahiri, S.D., et al., "Complementary expression of two plastid-localized sigma-like factors in maize," Plant Physiol., 123:883-894, (2000).
Kim, M., et al., "Detailed architechture of the barley chloroplast psbD-psbC blue light-responsive promoter," J. Biol. Chem., 274:4684-4692, (1999).
Kim, M., et al., "identification of a sequence-specific DNA binding factor required for transcription of the barley chloroplast . . . ," Plant Cell, 7:1445-1457, (1995).
Kestermann, M., et al., "Sequence and expression characteristics of a nuclear-encoded chloroplast sigma factor . . . ," Nuc. Acids Res., 26:2747-2753, (1998).
Jolly, S.O., et al., "Preferential transcription of cloned maize chloroplast DNA sequences by maize chloroplast RNA polymerase," Proc. Natl. Acad. Sci. USA, 77:822-826, (1980).
Isono, K., et al., "Leaf-specifically expressed genes for polypeptides destined for chloroplasts with domains of . . . ," Proc. Natl. Acad. Sci. USA, 94:14948-14953, (1997).
Iratni, R., et al., "Organ-specific transcription of the rrn operon. . . ," J. Biol. Chem., 272:13676-13682, (1997).
Hirvonen, C., et al., "Contributions of UP elements and the transcription factor FIS to expression from the seven rrn P1 promoters . . . ," J. Bact. 183:6305-6314, (2001).
Hakimi, M-A., et al., "Evolutionary conservation of C-terminal domains of primary sigma 70-type . . . ," J. Biol. Chem., 275:9215-9221, (2000).
Gruissem, W., et al., "Analysis of promoter regions for the spinach chloroplast rbcL, atpB and psbA genes," EMBO J., 4:3375-3383, (1985).
Eisermann, A., et al., "In vitro transcription and DNA binding characteristics of chloroplast and etioplast extracts from mustard . . . ," EMBO J., 9:3961-3987, (1990).

(Continued)

*Primary Examiner*—Anne Kubelik
(74) *Attorney, Agent, or Firm*—Kathleen D. Rigaut; Dann Dorfman Herrell & Skillman

(57) ABSTRACT

Prrn promoter elements for enhancing expression of heterologous molecules, including RNA and proteins in the plastids of higher plants are disclosed.

4 Claims, 8 Drawing Sheets

OTHER PUBLICATIONS

Dubell, A.N., et al., "Differential transcription of pea chloroplast genes during light-induced leaf development," Plant Physiol., 109:105-112, (1995).

Chun, L., et al., "Phytochrome A mediates blue light and UV-A-dependent chloroplast gene transcription in green leaves," Plant Physiol., 125:1957-1966, (2001).

Chan, C.L., et al., "The anti-initial transcribed sequence, a portable sequence that impedes promoter escape . . .," J. Biol. Chem., 276:38201-38209, (2001).

Bligny, M., et al., "Regulation of plastid rDNA transcription by interaction of CDF2 with two different RNA polymerases," EMBO J., 19:1851-1860, (2000).

Baumgartner, B.J., et al., "Plastid genes encoding the transcription/translation apparatus are differentially . . . ," Plant Physiol., 101:781-791, (1993).

Allison, L.A., et al., "Deletion of rpoB reveals a second distinct transcription system in plastids of higher plants," EMBO J., 15:2802-2809, (1996).

Allison, L.A., et al., "Light-responsive and transcription-enhancing elements regulate the plastid psbD core promoter," EMBO J., 14:3721-3730, (1995).

Aiyar, S.E., et al., "Upstream A-tracts increase bacterial promoter activity through interactions with . . . ," Proc. Natl. Acad. Sci. USA, 95:14652-14657, (1998).

Manna, F., et al., "A tRNA gene mapping within the chloroplast rDNA cluster is differentially expressed during the development . . . ," Nuc. Acids Res., 22:1712-1718, (1994).

* cited by examiner

A

Barley plastid promoters

```
              "-35"                           "-10"
PpsbA  . . . . . . . . . . . . . . [    ]TTGGTATATAGTCTATGT[    ] .
mutant . . . . . . . . . . . . . . [    ]TTGGTATATAGTCTATGT[    ] .

PrbcL  . . . . . . . . . . . . . . [    ]TATACCTATCAAAGAGTA[    ] .
mutant . . . . . . . . . . . . . . [    ]TATACCTATCAAAGAGTA[    ] .

AAG box              "-35"
PpsbD  . [AAAGAAGCATAAAGTAAGTAGACCTGACT][    ]GATGCCTCTATCCCC[    ] .
mutant . [AAAGAAGCATAAAGTAAGTAGACCTGACT][    ]GATGCCTCTATCCGC[    ] .
```

Tobacco PrrnP1

```
            RUA  "-35"                   "-10"
pJYS112 . . . [GTGGG][    ]TGAGGGGGCAGGGATGGC[    ]TCTGGGAGCGA . . .
pJYS174 . . . [GTGGC][    ]TGAGGGGGCAGGGATGGC[    ]TCTGGGAGCGA . . .
pJYS175 . . . [GTGGG][    ]TGAGGGGGCAGGGATGGC[    ]TCTGGGAGCCA . . .
pJYS199 . . . [GTGCG][    ]TGAGGGGGCAGGGATGGC[    ]TCTGGGAGCCA . . .
```

B

| | $t_1$ | $t_2$ | Relative Activity |
|---|---|---|---|
| pJYS112 | ● | ● | 100 |
| pJYS174 | ● | ● | 66.3 ± 12.6 |
| pJYS175 | ● | ● | 61.8 ± 4.89 |
| pJYS199 | ● | ● | 46.3 ± 5.10 |

SEQUENCE LISTING

```
<160> NUMBER OF SEQ ID NOS: 51

<210> SEQ ID NO 1
<211> LENGTH: 179
<212> TYPE: DNA
<213> ORGANISM: Nicotiana tabacum

<400> SEQUENCE: 1
ctcagcggta gagtgtcacc ttgacgtggt ggaagtcatc agttcgagcc tgattatccc      60
taagcccaat gtgagttttt ctagttggat ttgctccccc gccgtcgttc aatgagaatg     120
gataagaggc tcgtgggatt gacgtgaggg ggcagggatg gctatatttc tgggagcga     179

<210> SEQ ID NO 2
<211> LENGTH: 156
<212> TYPE: DNA
<213> ORGANISM: Escherichia Coli
```

```
<400> SEQUENCE: 2
gctgaacaat tattgcccgt tttacagcgt tacggcttcg aaacgctcga aaaactggca      60
gttttaggct gatttggttg aatgttgcgc ggtcagaaaa ttattttaaa tttcctcttg     120
tcaggccgga ataactccct ataatgcgcc accact                                156

<210> SEQ ID NO 3
<211> LENGTH: 112
<212> TYPE: DNA
<213> ORGANISM: Artificial Sequence
<220> FEATURE:
<223> OTHER INFORMATION: Prrn promoter derivative

<400> SEQUENCE: 3
gagctcatga gaatggataa gaggctcgtg ggattgacgt gagggggcag ggatggctat      60
atttctggga gcgaactccg ggcgaatatg aagcgcatgg atacaagaat tc             112

<210> SEQ ID NO 4
<211> LENGTH: 112
<212> TYPE: DNA
<213> ORGANISM: Artificial Sequence
<220> FEATURE:
<223> OTHER INFORMATION: Prrn promoter derivative

<400> SEQUENCE: 4
gagctctaca gaatggataa gaggctcgtg ggattgacgt gagggggcag ggatggctat      60
atttctggga gcgaactccg ggcgaatatg aagcgcatgg atacaagaat tc             112

<210> SEQ ID NO 5
<211> LENGTH: 112
<212> TYPE: DNA
<213> ORGANISM: Artificial Sequence
<220> FEATURE:
<223> OTHER INFORMATION: Prrn promoter derivative

<400> SEQUENCE: 5
gagctcatgt ctatggataa gaggctcgtg ggattgacgt gagggggcag ggatggctat      60
atttctggga gcgaactccg ggcgaatatg aagcgcatgg atacaagaat tc             112

<210> SEQ ID NO 6
<211> LENGTH: 112
<212> TYPE: DNA
<213> ORGANISM: Artificial Sequence
<220> FEATURE:
<223> OTHER INFORMATION: Prrn promoter derivative

<400> SEQUENCE: 6
gagctcatga gatacgataa gaggctcgtg ggattgacgt gagggggcag ggatggctat      60
atttctggga gcgaactccg ggcgaatatg aagcgcatgg atacaagaat tc             112

<210> SEQ ID NO 7
<211> LENGTH: 112
<212> TYPE: DNA
<213> ORGANISM: Artificial Sequence
<220> FEATURE:
<223> OTHER INFORMATION: Prrn promoter derivative

<400> SEQUENCE: 7
gagctcatga gaatgctaaa gaggctcgtg ggattgacgt gagggggcag ggatggctat      60
atttctggga gcgaactccg ggcgaatatg aagcgcatgg atacaagaat tc             112
```

```
<210> SEQ ID NO 8
<211> LENGTH: 112
<212> TYPE: DNA
<213> ORGANISM: Artificial Sequence
<220> FEATURE:
<223> OTHER INFORMATION: Prrn promoter derivative

<400> SEQUENCE: 8
gagctcatga gaatggattt caggctcgtg ggattgacgt gaggggggcag ggatggctat      60 atttctggga gcgaactccg ggcgaatatg aagcgcatgg atacaagaat tc              112

<210> SEQ ID NO 9
<211> LENGTH: 112
<212> TYPE: DNA
<213> ORGANISM: Artificial Sequence
<220> FEATURE:
<223> OTHER INFORMATION: Prrn promoter derivative

<400> SEQUENCE: 9
gagctcatga gaatggataa gtccctcgtg ggattgacgt gaggggggcag ggatggctat      60 atttctggga gcgaactccg ggcgaatatg aagcgcatgg atacaagaat tc              112

<210> SEQ ID NO 10
<211> LENGTH: 112
<212> TYPE: DNA
<213> ORGANISM: Artificial Sequence
<220> FEATURE:
<223> OTHER INFORMATION: Prrn promoter derivative

<400> SEQUENCE: 10
gagctcatga gaatggataa gagggaggtg ggattgacgt gaggggggcag ggatggctat      60 atttctggga gcgaactccg ggcgaatatg aagcgcatgg atacaagaat tc              112

<210> SEQ ID NO 11
<211> LENGTH: 112
<212> TYPE: DNA
<213> ORGANISM: Artificial Sequence
<220> FEATURE:
<223> OTHER INFORMATION: Prrn promoter derivative

<400> SEQUENCE: 11
gagctcatga gaatggataa gaggctccac ggattgacgt gaggggggcag ggatggctat      60 atttctggga gcgaactccg ggcgaatatg aagcgcatgg atacaagaat tc              112

<210> SEQ ID NO 12
<211> LENGTH: 112
<212> TYPE: DNA
<213> ORGANISM: Artificial Sequence
<220> FEATURE:
<223> OTHER INFORMATION: Prrn promoter derivative

<400> SEQUENCE: 12
gagctcatga gaatggataa gaggctcgtg cctttgacgt gaggggggcag ggatggctat      60 atttctggga gcgaactccg ggcgaatatg aagcgcatgg atacaagaat tc              112

<210> SEQ ID NO 13
<211> LENGTH: 112
<212> TYPE: DNA
<213> ORGANISM: Artificial Sequence
<220> FEATURE:
<223> OTHER INFORMATION: Prrn promoter derivative

<400> SEQUENCE: 13
```

```
gagctcatga gaatggataa gaggctcgtg ggaaacacgt gagggggcag ggatggctat        60
atttctggga gcgaactccg ggcgaatatg aagcgcatgg atacaagaat tc              112
```

<210> SEQ ID NO 14
<211> LENGTH: 112
<212> TYPE: DNA
<213> ORGANISM: Artificial Sequence
<220> FEATURE:
<223> OTHER INFORMATION: Prrn promoter derivative

<400> SEQUENCE: 14

```
gagctcatga gaatggataa gaggctcgtg ggattgtgct gagggggcag ggatggctat        60
atttctggga gcgaactccg ggcgaatatg aagcgcatgg atacaagaat tc              112
```

<210> SEQ ID NO 15
<211> LENGTH: 112
<212> TYPE: DNA
<213> ORGANISM: Artificial Sequence
<220> FEATURE:
<223> OTHER INFORMATION: Prrn promoter derivative

<400> SEQUENCE: 15

```
gagctcatga gaatggataa gaggctcgtg ggattgacga ctgggggcag ggatggctat        60
atttctggga gcgaactccg ggcgaatatg aagcgcatgg atacaagaat tc              112
```

<210> SEQ ID NO 16
<211> LENGTH: 112
<212> TYPE: DNA
<213> ORGANISM: Artificial Sequence
<220> FEATURE:
<223> OTHER INFORMATION: Prrn promoter derivative

<400> SEQUENCE: 16

```
gagctcatga gaatggataa gaggctcgtg ggattgacgt gacccggcag ggatggctat        60
atttctggga gcgaactccg ggcgaatatg aagcgcatgg atacaagaat tc              112
```

<210> SEQ ID NO 17
<211> LENGTH: 112
<212> TYPE: DNA
<213> ORGANISM: Artificial Sequence
<220> FEATURE:
<223> OTHER INFORMATION: Prrn promoter derivative

<400> SEQUENCE: 17

```
gagctcatga gaatggataa gaggctcgtg ggattgacgt gagggccgag ggatggctat        60
atttctggga gcgaactccg ggcgaatatg aagcgcatgg atacaagaat tc              112
```

<210> SEQ ID NO 18
<211> LENGTH: 112
<212> TYPE: DNA
<213> ORGANISM: Artificial Sequence
<220> FEATURE:
<223> OTHER INFORMATION: Prrn promoter derivative

<400> SEQUENCE: 18

```
gagctcatga gaatggataa gaggctcgtg ggattgacgt gaggggctc cgatggctat         60 atttctggga gcgaactccg ggcgaatatg aagcgcatgg atacaagaat tc              112
```

<210> SEQ ID NO 19
<211> LENGTH: 112
<212> TYPE: DNA

<213> ORGANISM: Artificial Sequence
<220> FEATURE:
<223> OTHER INFORMATION: Prrn promoter derivative

<400> SEQUENCE: 19
gagctcatga gaatggataa gaggctcgtg ggattgacgt gagggggcag gctaggctat    60
atttctggga gcgaactccg ggcgaatatg aagcgcatgg atacaagaat tc    112

<210> SEQ ID NO 20
<211> LENGTH: 112
<212> TYPE: DNA
<213> ORGANISM: Artificial Sequence
<220> FEATURE:
<223> OTHER INFORMATION: Prrn promoter derivative

<400> SEQUENCE: 20
gagctcatga gaatggataa gaggctcgtg ggattgacgt gagggggcag ggatccgtat    60
atttctggga gcgaactccg ggcgaatatg aagcgcatgg atacaagaat tc    112

<210> SEQ ID NO 21
<211> LENGTH: 112
<212> TYPE: DNA
<213> ORGANISM: Artificial Sequence
<220> FEATURE:
<223> OTHER INFORMATION: Prrn promoter derivative

<400> SEQUENCE: 21
gagctcatga gaatggataa gaggctcgtg ggattgacgt gagggggcag ggatggcata    60
atttctggga gcgaactccg ggcgaatatg aagcgcatgg atacaagaat tc    112

<210> SEQ ID NO 22
<211> LENGTH: 112
<212> TYPE: DNA
<213> ORGANISM: Artificial Sequence
<220> FEATURE:
<223> OTHER INFORMATION: Prrn promoter derivative

<400> SEQUENCE: 22
gagctcatga gaatggataa gaggctcgtg ggattgacgt gagggggcag ggatggctat    60
taatctggga gcgaactccg ggcgaatatg aagcgcatgg atacaagaat tc    112

<210> SEQ ID NO 23
<211> LENGTH: 112
<212> TYPE: DNA
<213> ORGANISM: Artificial Sequence
<220> FEATURE:
<223> OTHER INFORMATION: Prrn promoter derivative

<400> SEQUENCE: 23
gagctcatga gaatggataa gaggctcgtg ggattgacgt gagggggcag ggatggctat    60
attagaggga gcgaactccg ggcgaatatg aagcgcatgg atacaagaat tc    112

<210> SEQ ID NO 24
<211> LENGTH: 112
<212> TYPE: DNA
<213> ORGANISM: Artificial Sequence
<220> FEATURE:
<223> OTHER INFORMATION: Prrn promoter derivative

<400> SEQUENCE: 24
gagctcatga gaatggataa gaggctcgtg ggattgacgt gagggggcag ggatggctat    60
atttctccca gcgaactccg ggcgaatatg aagcgcatgg atacaagaat tc    112

<210> SEQ ID NO 25
<211> LENGTH: 112
<212> TYPE: DNA
<213> ORGANISM: Artificial Sequence
<220> FEATURE:
<223> OTHER INFORMATION: Prrn promoter derivative

<400> SEQUENCE: 25
gagctcatga gaatggataa gaggctcgtg ggattgacgt gagggggcag ggatggctat      60
atttctgggt cggaactccg ggcgaatatg aagcgcatgg atacaagaat tc            112

<210> SEQ ID NO 26
<211> LENGTH: 112
<212> TYPE: DNA
<213> ORGANISM: Artificial Sequence
<220> FEATURE:
<223> OTHER INFORMATION: Prrn promoter derivative

<400> SEQUENCE: 26
gagctcatga gaatggataa gaggctcgtg ggattgacgt gagggggcag ggatggctat      60
atttctggga gccttctccg ggcgaatatg aagcgcatgg atacaagaat tc            112

<210> SEQ ID NO 27
<211> LENGTH: 112
<212> TYPE: DNA
<213> ORGANISM: Artificial Sequence
<220> FEATURE:
<223> OTHER INFORMATION: Prrn promoter derivative

<400> SEQUENCE: 27
gagctcatga gaatggataa gaggctcgtg ggattgacgt gagggggcag ggatggctat      60
atttctggga gcgaagagcg ggcgaatatg aagcgcatgg atacaagaat tc            112

<210> SEQ ID NO 28
<211> LENGTH: 112
<212> TYPE: DNA
<213> ORGANISM: Artificial Sequence
<220> FEATURE:
<223> OTHER INFORMATION: Prrn promoter derivative

<400> SEQUENCE: 28
gagctcatga gaatggataa gaggctcgtg ggattgacgt gagggggcag ggatggctat      60
atttctggga gcgaactcgc cgcgaatatg aagcgcatgg atacaagaat tc            112

<210> SEQ ID NO 29
<211> LENGTH: 112
<212> TYPE: DNA
<213> ORGANISM: Artificial Sequence
<220> FEATURE:
<223> OTHER INFORMATION: Prrn promoter derivative

<400> SEQUENCE: 29
gagctcatga gaatggataa gaggctcgtg ggattgacgt gagggggcag ggatggctat      60
atttctggga gcgaactccg gcgcaatatg aagcgcatgg atacaagaat tc            112

<210> SEQ ID NO 30
<211> LENGTH: 112
<212> TYPE: DNA
<213> ORGANISM: Artificial Sequence
<220> FEATURE:
<223> OTHER INFORMATION: Prrn promoter derivative

```
<400> SEQUENCE: 30
gagctcatga gaatggataa gaggctcgtg ggattgacgt gaggggggcag ggatggctat      60 atttctggga gcgaactccg ggcgttaatg aagcgcatgg atacaagaat tc             112

<210> SEQ ID NO 31
<211> LENGTH: 30
<212> TYPE: DNA
<213> ORGANISM: Hordeum vulgare

<400> SEQUENCE: 31
ttgacattgg tatatagtct atgttatact                                       30

<210> SEQ ID NO 32
<211> LENGTH: 30
<212> TYPE: DNA
<213> ORGANISM: Hordeum vulgare

<400> SEQUENCE: 32
ttgacattgg tatatagtct atgtaataca                                       30

<210> SEQ ID NO 33
<211> LENGTH: 30
<212> TYPE: DNA
<213> ORGANISM: Hordeum vulgare

<400> SEQUENCE: 33
ttgcgctata cctatcaaag agtatacaat                                       30

<210> SEQ ID NO 34
<211> LENGTH: 30
<212> TYPE: DNA
<213> ORGANISM: Hordeum vulgare

<400> SEQUENCE: 34
ttgcgctata cctatcaaag agtaaacaaa                                       30

<210> SEQ ID NO 35
<211> LENGTH: 58
<212> TYPE: DNA
<213> ORGANISM: Hordeum vulgare

<400> SEQUENCE: 35
aaagaagcat aaagtaagta gacctgactc cttgaatgat gcctctatcc gctattct        58

<210> SEQ ID NO 36
<211> LENGTH: 58
<212> TYPE: DNA
<213> ORGANISM: Hordeum vulgare

<400> SEQUENCE: 36
aaagaagcat aaagtaagta gacctgactc cttgaatgat gcctctatcc gcaattca        58

<210> SEQ ID NO 37
<211> LENGTH: 47
<212> TYPE: DNA
<213> ORGANISM: Nicotiana tabacum

<400> SEQUENCE: 37
gtgggattga cgtgaggggg cagggatggc aatatatctg ggagcga                    47

<210> SEQ ID NO 38
<211> LENGTH: 233
```

```
<212> TYPE: DNA
<213> ORGANISM: Nicotiana tabacum

<400> SEQUENCE: 38
ctaagcccaa tgtgagtttt tctagttgga tttgctcccc cgccgtcgtt caatgagaat      60
ggataagagg ctcgtgggat tgacgtgagg gggcaggggat ggctatattt ctgggagcga    120
actccgggcg aatatgaagc gcatggatac aagttatgcc ttggaatgaa agacaattcc    180
gaatccgctt tgtctacgaa caaggaagct ataagtaatg caactatgaa tct           233

<210> SEQ ID NO 39
<211> LENGTH: 237
<212> TYPE: DNA
<213> ORGANISM: Oryza Sativa

<400> SEQUENCE: 39
ctaaacccaa tgtgagtttt ttctattttg acttactccc cccgccacga tcgaacggga     60
atggataaga ggcttgtggg attgacgtga tagggtaggg ttggctatac tgctggtggc   120
gaactccagg ctaataatct gaagcgcatg gatacaagtt atccttggaa ggaaagacaa   180
ttccgaatcc gctttgtcta cgaataagga agctataagt aatgcaacta tgaatct      237

<210> SEQ ID NO 40
<211> LENGTH: 236
<212> TYPE: DNA
<213> ORGANISM: Zea mays

<400> SEQUENCE: 40
ctaaacctaa tgtgagtttt ttctattttg acttactccc ccaccacgat cgaacgggaa     60
tggataggag gcttgtggga ttgacgtgat agggtagggt tggctatact gctggtggcg   120
aactccaggc taataatctg aagcgcatgg atacaagtta tccttggaag gaaagacaat   180
tccgaatccg ctttgtctac gaataaggaa gctataagta atgcaactat gaatct       236

<210> SEQ ID NO 41
<211> LENGTH: 233
<212> TYPE: DNA
<213> ORGANISM: Spinacea oleracea

<400> SEQUENCE: 41
ctaaacccaa cgtcagtttt tctattttga cttgctcccc cgccgtgatt gaatgagaat     60
gaataagagg ctcgtgggat tgacgtgagg gggtagggat ggctatattt ctgggagcga   120
actccaggcg aatatgaagc gcatggatac aagttatgcc ttggaatgaa agacaattcc   180
gaatccgctt tgtctacgaa caaggaagct ataagtaatg caactatgaa tct           233

<210> SEQ ID NO 42
<211> LENGTH: 234
<212> TYPE: DNA
<213> ORGANISM: Daucus carota

<400> SEQUENCE: 42
ctaaatccca atgggagttt ttctattttg atttgctccc ccgccgtgat tgaacgagaa     60
tcaagaagag gctcgtggga ttgacgtgag ggggcaggga tggctatatt ctgggagcg    120 aactccgggc gaatatgaag cgcatggata caagttaggc cttggaatga agacaattc    180 cgaatccgct tgtctacga acaaggaagc tataagtaat gcaactatga atct           234

<210> SEQ ID NO 43
```

```
<211> LENGTH: 237
<212> TYPE: DNA
<213> ORGANISM: Arabidopsis thaliana

<400> SEQUENCE: 43
ctaaacccaa tgaatgtgag tttttctatt ttgacttgct ccctcgctgt gatcgaataa      60
gaatggataa gaggctcgtg ggattgacgt gaggggtag gggtagctat atttctggga     120
gcgaactcca tgcgaatatg aagcgcatgg atacaagtta tgacttggaa tgaaagacaa    180
ttccgaatca gctttgtcta cgaagaagga agctataagt aatgcaacta tgaatct       237

<210> SEQ ID NO 44
<211> LENGTH: 227
<212> TYPE: DNA
<213> ORGANISM: Glycine max

<400> SEQUENCE: 44
ctaaacccaa tgtaagtttt tctatttgta tgccgtgatc gaataataat tgagaatgga     60
taagaggctc gtgggattac acgaggggtg gggggctat atttctggga gcgaactcca    120
gtcgaatatg aagcgcctgg atacaagtta tgccttggaa tggaagagaa ttccgaatca   180
gctttgtcta cgaacaagga agctataagt aatgcaacta ggaatct                  227

<210> SEQ ID NO 45
<211> LENGTH: 264
<212> TYPE: DNA
<213> ORGANISM: Pisum sativum

<400> SEQUENCE: 45
ctaaacccaa tatcaatttt tccatttgag gacgagatcc aatctgagta gataagagga     60
tagggagttg acacaagggg gggtaaggcc atataatatt tatgggaggc aactccgggc   120
gaatagtaag cccatggata caagtcaagt tatgtcttct cagttcagta actgaaatca   180
aatttaagtt cagtaaatga aatcaaattc cgaatcagct ttgtctagaa acaaggaagc   240
tataagtaat gcaactagga agct                                           264

<210> SEQ ID NO 46
<211> LENGTH: 33
<212> TYPE: DNA
<213> ORGANISM: Artificial Sequence
<220> FEATURE:
<223> OTHER INFORMATION: ribosome binding site

<400> SEQUENCE: 46
ctcgagaatt cagttgtagg gagggatcca tgg                                   33

<210> SEQ ID NO 47
<211> LENGTH: 10
<212> TYPE: PRT
<213> ORGANISM: homo sapien

<400> SEQUENCE: 47

Glu Gln Lys Leu Ile Ser Glu Glu Asp Leu
 1               5                  10

<210> SEQ ID NO 48
<211> LENGTH: 21
<212> TYPE: DNA
<213> ORGANISM: Artificial Sequence
<220> FEATURE:
<223> OTHER INFORMATION: primer
```

```
<400> SEQUENCE: 48
tcacctgccg aatcaactag c                                              21

<210> SEQ ID NO 49
<211> LENGTH: 20
<212> TYPE: DNA
<213> ORGANISM: Artificial Sequence
<220> FEATURE:
<223> OTHER INFORMATION: primer

<400> SEQUENCE: 49
gacttccctt gcctacattg                                                20

<210> SEQ ID NO 50
<211> LENGTH: 6
<212> TYPE: DNA
<213> ORGANISM: Artificial Sequence
<220> FEATURE:
<223> OTHER INFORMATION: PrrnP1 conserved essential sequence

<400> SEQUENCE: 50 gtggga                                                                6

<210> SEQ ID NO 51
<211> LENGTH: 63
<212> TYPE: DNA
<213> ORGANISM: Artificial Sequence
<220> FEATURE:
<223> OTHER INFORMATION: mutant Prrn

<400> SEQUENCE: 51
gagctcttct ccgaggtggg attgacgtga gggggctccc taggctatat tagagggagc    60
gaa                                                                  63
```

PLASTID RRNA OPERON PROMOTER ELEMENTS FOR CONSTRUCTION OF CHIMERIC PROMOTERS FOR TRANSGENE EXPRESSION

This application claims priority to U.S. Provisional Application 60/433,302, filed Dec. 13, 2002. The entire disclosure of the '302 application is incorporated by reference herein.

Pursuant to 35 U.S.C. §202(c), it is acknowledged that the U.S. Government has certain rights in the invention described, which was made in part with funds from the National Science Foundation, Grant Number MCB 99-05043.

FIELD OF THE INVENTION

This invention relates to the fields of molecular biology and the creation of transgenic plants. More specifically, the present invention provides novel Prrn based promoter constructs useful for driving high level expression of heterologous proteins in plastids.

BACKGROUND OF THE INVENTION

Several patent documents and research articles are cited throughout this application in order to more fully describe the state of the art to which this invention pertains. The disclosure of each of these citations is incorporated by reference herein.

The most abundant transcripts in plastids are the ribosomal RNAs (rRNAs). The biosynthesis of plastid rRNA is highly regulated during development at both the transcriptional and posttranscriptional levels. In barley, rates of rrn transcription vary by 50-fold and rRNA stability by 35-fold in response to developmental and environmental cues (Baumgartner et al., 1993). Rates of rrn transcription were induced 10-fold in pea and tobacco chloroplasts in response to light (DuBell and Mullet, 1995; Shiina et al., 1998; Chun et al., 2001). Transcription of the plastid ribosomal RNA operon (rrn) in higher plants is from diverse promoters. The rrn operon in tobacco is transcribed by the multisubunit, plastid encoded RNA polymerase (PEP) from a sigma-70 type promoter (PrrnP1)(Vera and Sugiura, 1995) as in most higher plants including maize (Strittmatter et al., 1985), pea (Sun et al., 1989), carrot (Manna et al., 1994), rice (Silhavy and Maliga, 1998), barley (Hubschmann and Borner, 1998) and *Arabidopsis* (Sriraman et al., 1998a). In tobacco, in addition to the PrrnP1 PEP promoter, rrn is transcribed from a second promoter, PrrnP2, recognized by the nuclear-encoded plastid RNA polymerase (NEP) (Vera and Sugiura, 1995; Allison et al., 1996). In spinach, transcription of rrn initiates in the same region, but from a promoter distinct from the PrrnP1 or the PrrnP2 promoters. This promoter, Pc, is the only promoter upstream of the rrn operon in spinach and is probably also recognized by the NEP (Iratni et al., 1997; Bligny et al., 2000). Pc is utilized as a second rrn promoter in *Arabidopsis* (Sriraman et al., 1998a), and is recognized in mustard chloroplasts (Pfannschmidt and Link, 1997).

To identify promoter elements important for PrrnP1 function, promoter dissection was carried out in vivo and in vitro. In vivo dissection was carried out by studying expression of uidA reporter genes from an ordered set of PrrnP1 promoter derivatives (Staub and Maliga, 1993; Allison and Maliga, 1995). In vitro dissection was carried out by measuring transcript accumulation from mini-genes which consist of a PrrnP1 promoter derivative and transcription terminators (Jolly and Bogorad, 1980; Link, 1984; Gruissem and Zurawski, 1985; Orozco et al., 1985). In vivo dissection of the plastid rrn operon promoter indicates that sequences upstream of the conserved −35 box are important for promoter function.

SUMMARY OF THE INVENTION

It is an object of the invention to identify and characterize promoter sequence elements which are responsible for the high transcription level of the plastid rnn operon. Such sequence elements are useful for the construction of chimimeric promoters for driving transgene expression from the plastid genome. Also disclosed are novel, isolated Prnn promoter derivatives that are useful for driving the expression of transgenes. The Prnn promoter derivatives can be used to advantage to enhance or decrease expression levels of heterologous molecules relative to that observed using a wild type Prnn promoter.

In one embodiment, an isolated nucleic acid sequence for promoting expression of heterologous molecules in the plastids of higher plants selected from the group of Prrn derivative sequences having SEQ ID NOS: 4–30 are provided. Such promoter derivatives can be operably linked to a sequence encoding a heterologous molecule of interest or precursor thereof. Heterologous molecules of interest include proteins and RNAs, such as siRNA. Vectors comprising the aforementioned chimeric sequences are also encompassed by the invention. In a preferred embodiment, a transgenic plant comprising such a vector is provided.

In yet another embodiment of the invention, an isolated nucleic acid sequence for promoting expression of heterologous molecules in the plastids of higher plants comprising mutations which mimimize homologous recombination at the Prrn operon having the sequence of SEQ ID NO: 51 is disclosed. As above, this sequence can be operably linked to a sequence encoding a heterologous molecule of interest or precursor thereof. Also encompassed by the invention are vectors suitable for expression in plastids comprising SEQ ID NO: 51 operably linked to a sequence encoding a heterologous molecule of interest. Finally, transgenic plants comprising such a vector are within the scope of the present invention.

In another aspect, a chimeric promoter for expression of transgenes in the plastids of higher plants, comprising at least one Prrn transcription modulating element (PTME) operably linked to a core promoter selected from the group consisting of those provided in Table I are provided. In preferred embodiments, the PTME is SEQ ID NO: 50 and the promoter elements are either rbcl and or psbD. Such chimeric promoters are further operably linked to a sequence encoding a heterologous molecule of interest. Vectors and plants comprising the aforementioned constructs are also within the scope of the invention.

BRIEF DESCRIPTION OF THE DRAWINGS

FIG. 2A: Tobacco PrrnP1 promoter deletion derivatives. Nucleotide position is given relative to the transcription initiation site (+1; horizontal arrows). The position of the conserved −35 and −10 elements are marked. Plasmid names are listed on the left. FIG. 2B: Plastid transformation vector with Left and Right targeting sequences, the selectable marker (aada) and uida reporter gene. Position of plastid genes rrn16, trnv and rpsl2/7, and relevant restriction sites is indicated. Horizontal arrows mark gene orientation. FIG. 2C: RNA gel blot to test steady-state levels of uida mRNA in transplastomic plants. Probing for the cytoplasmic 25S rRNA is used as the loading control.

FIG. 3A: Diagram of construct for testing in vitro promoter activity. Arrows $t_1$ and $t_2$ denote the two transcripts terminating within the his (This) and thr (Tthr) attenuators. FIG. 3B Tobacco PrrnP1 promoter deletion derivatives. Nucleotide position is given relative to the transcription initiation site (+1; horizontal arrows). The position of the conserved −35 and −10 elements are marked. Plasmid names are listed on the right. FIG. 3C: Autoradiograph of the in vitro transcripts and relative quantities. Values were determined as described in Methods and are averages of three experiments.

FIG. 4A: DNA sequence of Prrn promoter derivatives (SEQ ID NOS: 3–30). Plasmid names with mutated nucleotide positions are listed on the left. On top a horizontal arrow marks the positions of multiple transcription initiation sites (TIS) and vertical arrowheads mark the −64, +17 and +37 positions relative to the TIS marked +1. Relevant cloning sites are labeled. The conserved −35 and −10 promoter elements are boxed. Dots in the alignment represent identical sequences. Non-plastid nucleotides are in lower case, mutated nucleotides are in bold. FIG. 4B: Autoradiograph of the in vitro transcripts and relative quantities. The origin of the $t_1$ and $t_2$ transcripts is explained in FIG. 3. Signals of transcripts derived from the three initiation sites do not resolve. Bars represents the sum of signals of the $t_1+t_2$ transcripts relative to clone pJYS112 (100%). FIG. 4B was obtained by merging two independently obtained data sets. Values for clones on the left (plasmids pJYS15 through pJYS124) and on the right (pJYS112 through pJYS183) were normalized for their own control (pJYS112; 100%; black bar). Values were determined as described in Methods and are averages of three experiments.

FIGS. 5A and 5B show the strategy used to assess the contribution of the −10 region to promoter strength. FIG. 5A: DNA sequence of wild-type and mutant −10 region in barley (Kim et al., 1999) SEQ ID NOS: 31–36) and tobacco (this study) (nucleotides 28 to 74 of SEQ ID NO: 3, nucleotides 28 to 74 of SEQ ID NO: 21, nucleotides 28 to 74 of SEQ ID NO: 22 and SEQ ID NO: 37) plastid promoters. FIG. 5B: Autoradiograph of the in vitro transcripts and relative transcription activity of the tobacco PrrnP1 derivatives. Values were determined as described in Methods and are averages of three experiments.

FIG. 6A: Factor-independent activation of PrrnB1 transcription. Depicted here is sigma interaction with the RUA-35 region. Note, however, that the actual subunit involved in the interaction may be a different subunit. Identified in the Figure are the α (αCTD, αNTD), β, β', β" and σ subunits, and the RUA, −35 and −10 promoter elements. FIG. 6B: Factor-dependent activation of PrrnP1 transcription by activator bound to RUA.

FIG. 7 shows the alignment of the trnV and rrn Intergenic Region in the Plastid Genome of Monocot and Dicot Species. Data are shown for tobacco (N. tabacum, Nt; SEQ ID NO: 38), rice (O. sativa, Os; SEQ ID NO:39), maize (Zea mays, Zm; SEQ ID NO:40), spinach (S. oleracea, So; SEQ ID NO:41), carrot (D. carota, Dc; SEQ ID NO:42), Arabidopsis (A. thaliana, At; SEQ ID NO:43), soybean (G. max, Gm; SEQ ID NO:44) and pea (P. sativum, Ps; SEQ ID NO:45). The ends of the structural genes for trnV and rrn are bracketed. The RUA, −35 and −10 conserved promoter elements are boxed. Horizontal arrows mark transcription initiation sites from Pc, PrrnP1 (P1) and PrrnP2 (P2) promoters. Vertical arrows denote position of tobacco processing sites. Dashes represent gaps in the alignment. Conserved nucleotide positions are denoted by asterisk below the alignment.

DETAILED DESCRIPTION OF THE INVENTION

Figure 1:
FIG. 1 shows the alignment of the tobacco plastid (Nt) (SEQ ID NO: 1) and *E. coli* (Ec) (SEQ ID NO: 2) rRNA operon upstream regions. Nucleotide position is given relative to the transcription initiation site (TIS; +1; horizontal arrows). The Fis binding sites (bold), and the promoter recognition region, including the UP element and the conserved −35 and −10 elements, are marked. For tobacco, the 3' end of trnV gene is also indicated.

Expression of the plastid rRNA operon (rrn) during development is highly regulated at the level of transcription. The plastid rrn operon in most higher plant species is transcribed by the PEP, the multisubunit plastid RNA polymerase from PrrnP1, a sigma-70 type promoter with conserved −10 and −35 core promoter elements. To identify functionally important sequences, the tobacco PrrnP1 was dissected in vivo and in vitro. Based on the in vivo deletion analysis, sequences upstream of nucleotide −83 do not significantly contribute to promoter function.

The more detailed in vitro dissection described herein identified an RUA (rRNA upstream activator), a conserved 6 bp sequence directly upstream of the −35 core promoter element responsible for enhanced transcription from the PrrnP1 promoter core. Furthermore, the in vitro dissection revealed that the −35 hexamer, but not the −10 element, is crucial for promoter activity. Mutagenesis of sequences downstream of the transcription start site lead to enhanced in vitro transcription. We propose that sigma interaction with the −10 element in PrrnP1 is in part replaced by direct PEP-RUA (protein-DNA) interaction or by protein-protein interaction between the PEP and an RUA-binding transcription factor.

The following definitions are provided to aid in understanding the subject matter regarded as the invention.

"Heteroplastomic" refers to the presence of a mixed population of different plastid genomes within a single plastid or in a population of plastids contained in plant cells or tissues.

"Homoplastomic" refers to a pure population of plastid genomes, either within a plastid or within a population contained in plant cells and tissues. Homoplastomic plastids, cells or tissues are genetically stable because they contain only one type of plastid genome. Hence, they remain homoplastomic even after the selection pressure has been removed, and selfed progeny are also homoplastomic. For purposes of the present invention, heteroplastomic populations of genomes that are functionally homoplastomic (i.e., contain only minor populations of wild-type DNA or transformed genomes with sequence variations) may be referred to herein as "functionally homoplastomic" or "substantially homoplastomic." These types of cells or tissues can be readily purified to a homoplastomic state by continued selection.

"Plastome" refers to the genome of a plastid.

"Transplastome" refers to a transformed plastid genome.

Transformation of plastids refers to the stable integration of transforming DNA into the plastid genome that is transmitted to the seed progeny of plants containing the transformed plastids.

"Selectable marker gene" refers to a nucleic acid sequence that upon expression confers a phenotype by which successfully transformed plastids or cells or tissues carrying the transformed plastid can be identified.

"Transforming DNA" refers to homologous DNA, or heterologous DNA flanked by homologous DNA, which when introduced into plastids becomes part of the plastid genome by homologous recombination.

An alternative type of transforming DNA refers to a DNA which contains recombination site sequences for a site-specific recombinase or integrase. Insertion of this type of DNA is not dependent on the degree of homology between the transforming DNA and the plastid to be transformed but rather is catalyzed by the action of the recombinase or integrase on the first and second recombination sites.

"Operably linked" refers to two different regions or two separate nucleic acid sequences spliced together in a construct such that both regions will function to promote gene expression and/or protein translation.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

The phrase "heterologous molecule" refers to a molecule which is produced in the plant following introduction of a nucleic acid of the invention. Such molecules include RNA, (e.g., siRNA) and proteins.

The terms "percent similarity", "percent identity" and "percent homology" when referring to a particular sequence are used as set forth in the University of Wisconsin GCG software program.

The term "functional" as used herein implies that the nucleic or amino acid sequence is functional for the recited assay or purpose.

The phrase "consisting essentially of" when referring to a particular nucleotide or amino acid means a sequence having the properties of a given SEQ ID No:. For example, when used in reference to an amino acid sequence, the phrase includes the sequence per se and molecular modifications that would not affect the basic and novel characteristics of the sequence.

The phrase Prnn transcription modulating element (PTME) as used herein refers to elements identified in accordance with the invention and include the RUA, the −35 hexamer, the G-patch, −10 region, the spacer between the −10 and TIS and the ITS region. See FIG. 4.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the production of a polypeptide coding sequence in a host cell or organism. Such expression signals may be combined such that production of said polypeptide occurs transiently or is produced stably over the life of the cell.

The term "oligonucleotide," as used herein refers to primers and probes of the present invention, and is defined as a nucleic acid molecule comprised of two or more ribo or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single stranded or double stranded. The exact length of the probe will depend upon many factors, including temperature, source of probe and use of the method. For example, for diagnostic applications, depending on the complexity of the target sequence, the oligonucleotide probe typically contains 15 25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non complementary nucleotide fragment may be attached to the 5' or 3' end of the probe, with the remainder of the probe sequence being complementary to the target strand. Alternatively, non complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single stranded or double stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield an primer extension product. The primer may vary in length depending on the particular conditions and requirement of the application. For example, in diagnostic applications, the oligonucleotide primer is typically 15 25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non complementary nucleotide sequence may be attached to the 5' end of an otherwise complementary primer. Alternatively, non complementary bases may be interspersed within the oligonucleotide primer sequence, provided that the primer sequence has sufficient complementarity with the sequence of the desired template strand to functionally provide a template primer complex for the synthesis of the extension product.

Amino acid residues described herein are preferred to be in the "L" isomeric form. However, residues in the "D" isomeric form may be substituted for any L amino acid residue, provided the desired properties of the polypeptide are retained. All amino acid residue sequences represented herein conform to the conventional left-to-right amino terminus to carboxy terminus orientation.

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, to that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino or carboxy terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c myc epitope, transmembrane epitope of the influenza A virus hemaglutinin protein, protein A, cellulose binding domain, calmodulin binding protein, maltose binding protein, chitin binding domain, glutathione S transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by, the trained artisan, and are contemplated to be within the scope of this definition.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radioimmunoassay, or by calorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion, biolistic bombardment and the like.

A "clone" or "clonal cell population" is a population of cells derived from a single cell or common ancestor by mitosis.

A "cell line" is a clone of a primary cell or cell population that is capable of stable growth in vitro for many generations.

The following Examples are provided to describe certain embodiments of the invention. They are not intended to limit the invention in any way.

EXAMPLE I

The following materials and methods are provided to facilitate the practice of the present invention.

Alignment of rrn Promoter Regions

E. coli and tobacco promoter comparison was made using the E. coli genomic sequences U.S. Pat. Nos. 4,163,793–4,163,947 (accession NC_000913) and tobacco plastid sequences 102,472–102,560 (accession Z00044). Plant plastid trnv/rrn intergenic region comparisons were made using the following sequences: rice, 91,065–91,301 (accession X15901); maize, 94,931–95,166 (accession X86563); spinach, 97,717–97,949 (accession AJ400848.1); Arabidopsis, 100,778–101,014 (accession AP000423); tobacco, 102531–102,763 (Accession Z00044); carrot, 317–550 (accession X78534); soybean, complement of 1477–1703 (Accession X07675); and pea, 70–333 (accession M30826). Sequence comparisons were made using the ClustalW program of the Sequence Interpretation tools section of GenomeNet.

Plasmids for In Vitro Assays

Plasmids for the in vitro assay were obtained by cloning PCR-amplified promoter derivatives (SacI-EcoRI fragments) into plasmid pKL23, a pBluescript KSII+ plasmid derivative carrying two bacterial transcription terminators downstream of suitable (SacI-EcoRI) restriction sites (Liere and Maliga, 1999). The promoter fragments were designed to have a SacI site at 5'end and an EcoRI site at 3'end. The 5'ends correspond to the following nucleotides of the tobacco plastid genome (Wakasugi et al., 1998): Prrn-175, 102,475; Prrn-105, 102,542; Prrn-83, 102,564; Prrn-64, 102,583; Prrn-38, 102,609; Prrn+37, 102,683; Prrn+17, 102,663; and Prrn+12, 102,658. The endpoints of the 5' deletion at Prrn-175 encoded part of the cloning site SacI, whereas endpoints of the 3' deletions Prrn+37, Prrn+17 and Prrn+12 encoded part of the EcoRI site. For scanning mutagenesis, 3 bp mutations were incorporated in the respective PCR primers. The DNA sequence of the promoter derivatives was confirmed by sequencing.

Plastid Transformation Vectors

Figure 2:
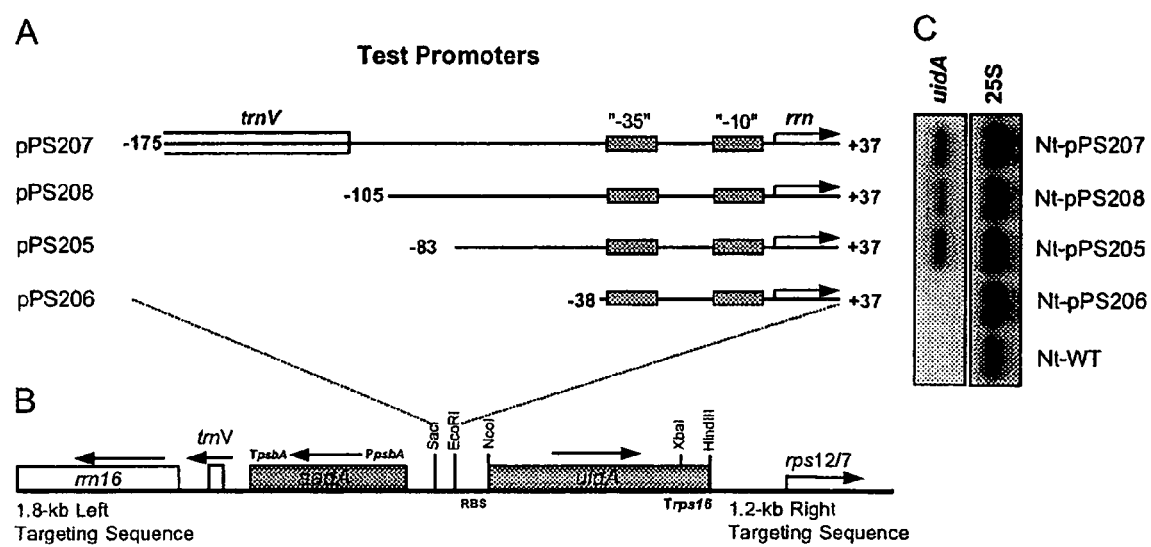
FIGS. 2A, 2B and 2C show the strategy used for identification of PrrnP1 Upstream Promoter.

Plasmid pPS205 contains a chimeric uidA reporter gene as a SacI-HindIII fragment in a pPRV111A plastid vector (FIG. 2). Plasmid pPS205 is a plasmid pPS6 derivative (Sriraman et al., 1998b). The chimeric uidA gene consists of: Between the SacI and EcoRI sites, the test promoter fragment PrrnP1 −83/+37 with +1 being the transcription start site (FIG. 1); Between the EcoRI and the NcoI sites, a synthetic ribosome binding site with the following sequence 5'-CTCGAGAAT-TCAGTT GTAGGGAGGGATCCATGG-3' SEQ ID NO: 46; Between the NcoI and XbaI sites, the uidA coding region with an N-terminal c-myc tag corresponding to amino acids 410–419 (EQKLISEEDL; SEQ ID NO: 47) within the carboxy terminal domain of the human c-myc protein; Between the XbaI and HindIII sites the 3' untranslated region of the rps16 ribosomal protein gene (Trps16). The SacI-EcoRI promoter fragment of pPS205 was replaced with PrrnP1 −38/+37 to obtain pPS206, with PrrnP1 −175/+37 to obtain pPS207 and with PrrnP1 −105/+37 to obtain pPS208. The SacI-EcoRI fragments for plasmids pPS205 through pPS208 were obtained by PCR amplification as described for the construction of in vitro test plasmids.

In Vitro Transcription Assay

High salt extracts were prepared from Percoll step gradient-purified chloroplasts of young leaves of 6–8 week old tobacco (Nicotiana tabacum cv. Petit Havana) plants (Orozco et al., 1986). The final ammonium sulfate pellets were resuspended at a ratio of 1 ml DEAE buffer per 7.5 mg of chlorophyll. For the in vitro transcription reaction, supercoiled plasmid DNA (0.9376 pmole) was incubated at 30° C. for 20 min in a 20 µl reaction mix consisting of 8.0 µl plastid protein extract (equiv. ~9.0×10$^7$ chloroplasts), 12 mM HEPES-KOH pH 8.0, 10 mM MgCl$_2$, 40 mM KCl, 10 mM DTT, 500 µM each of GTP and CTP and 50 µM each of ATP and UTP and 5.4 u of RNA guard (Amersham Biosciences, Piscataway, N.J.), 17.21–24.25 µCi of $\alpha^{32}$P-UTP (6000 Ci-mmole$^{-1}$; Perkin Elmer Life Sciences, Boston, Mass.) was included to allow detection and quantitation of transcribed products. The reactions were stopped with the addition of 115 µl of RNA extraction mix (0.36 M NaCl, 20 mM EDTA, 10 mM Tris pH 8 and 1% SDS), 15 µl of 5 M NH$_4$OAc, 40 µg of yeast tRNA, and extracted with a 1:1 mix of phenol and chloroform. 120 µl of the supernatant was precipitated with 150 µl isopropanol. The final pellet was resuspended in 6 µl of loading dye (Ambion, Austin, Tex.) and half was loaded on a 6.0% Long Ranger gel (BioWhittaker Molecular Applications, Rockland, Me.). Relative transcript levels were quantitated using a PhosphorImager and the ImageQuant program (Amersham Biosciences, Piscataway, N.J.) with values normalized. The Phoshoimager values of $t_1$ and $t_2$ were first individually normalized for background signals from each lane, divided by the number of predicted U residues (47 and 59, respectively) in their transcripts and then subsequently added together.

Plastid Transformation

Plastid transformation and characterization of transplastomic lines was carried out as described (Svab and Maliga, 1993).

RNA Gel Blot Analysis

Total cellular RNA was extracted from plants grown in sterile culture (MS salts, 3% sucrose, 0.7% agar; 18 hr light and 6 hr dark cycle) by the method of Stiekema (Stiekema et al., 1988). RNA (1 µg per lane) was separated in 1.2% agarose, formaldehyde-MOPS gels and blotted by the Posiblot transfer apparatus (Stratagene, La Jolla, Calif.) onto Hybond N membranes (Amersham Biosciences, Piscataway, N.J.). The 25S rDNA probe was PCR amplified using primers '5-TCACCTGCCGAATCAACTAGC-3' (SEQ ID NO: 48) and '5-GACTTCCCTTGCCTACATTG-3' (SEQ ID NO: 49) and total tobacco cellular DNA as template (Dempsey et al., 1993). The uida probe was the NcoI/XbaI fragment from plasmid pPS6 (Sriraman et al., 1998b). Radioactive probes were prepared using the Ready-To-Go DNA labeling beads (Amersham Biosciences, Piscataway, N.J.) and $\alpha^{32}$P-dCTP. Blots were hybridized at 65° C. in Rapid Hybridization buffer (Amersham Biosciences, Piscataway, N.J.).

Upon request, all novel material described in this publication will be made available in a timely manner for non-commercial research purposes.

Examination of the rrn Upstream Region for Potential Regulatory Sequences

Promoter elements regulating transcription, at least in the case of the plastid psbD promoter are localized upstream of the −35 promoter core (Allison and Maliga, 1995; Kim and Mullet, 1995; Kim et al., 1999; Thum et al., 2001). Therefore, we have searched for potential regulatory elements between the plastid trnv gene and the rrn coding region. Given conservation of the E. coli and plastid PEP transcription machineries, we used the well-characterized E. coli rrnB P1 promoter regulatory sequences as a guide (FIG. 1)(Ross et al., 1993).

Two types of cis elements are responsible for the E. coli rrnB P1 promoter strength. One is the UP element, a 20 bp AT-rich region directly upstream (−40 to −60) of the promoter core. The UP element interacts directly with the E. coli RNA polymerase α subunit C-terminal domain increasing the basal promoter activity by 30–60 fold (Ross et al., 1993; Rao et al., 1994; Aiyar et al., 1998; Gourse et al., 2000). The tobacco rrn P1 lacks an AT-rich sequence in the region corresponding to the E. coli UP element. A second type of E. coli cis regulatory element is the Fis binding site. Fis is a 11.2 kDa DNA binding, DNA bending, highly conserved protein in bacteria originally identified as Factor for inversion stimulation (Ross et al., 1990). The spacing between the Fis binding sites differs among the 7 ribosomal RNA P1 promoters of E. coli, yet all contribute albeit to different extents to promoter activity (Hirvonen et al., 2001). The positions of the E. coli Fis binding sites were considered when designing the deletion endpoints for the in vivo PrrnP1 promoter analysis.

Dissection of the PrrnP1 Upstream Region In Vivo

In vivo testing of promoter derivatives is the most reliable approach to identify promoter elements. Thus, we prepared an ordered set of PrrnP1 promoter deletion derivatives that were fused with the uida reporter gene (FIG. 2A). The reporter genes were cloned into a plastid transformation vector in which uida is linked to a selectable spectinomycin resistance (aada) gene. The transgenes were then introduced into the tobacco plastid genome. Four transplastomic lines were obtained in which uida is expressed from a PrrnP1 derivative (FIG. 2A).

RNA gel blot analysis was carried out to determine uida mRNA accumulation in the leaves of the transgenic plants. Results shown in FIG. 2 indicate that deletion of the −175 to −83 region has no effect on uida transcription. However, deletion of nucleotides between −83 to −38 completely eliminated promoter activity as no signal could be detected even on over-exposed films (data not shown). Thus, based on the in vivo deletion analysis, there are no PrrnP1 promoter elements upstream of nucleotide −83.

Dissection of the PrrnP1 Upstream Region In Vitro

Figure 3:
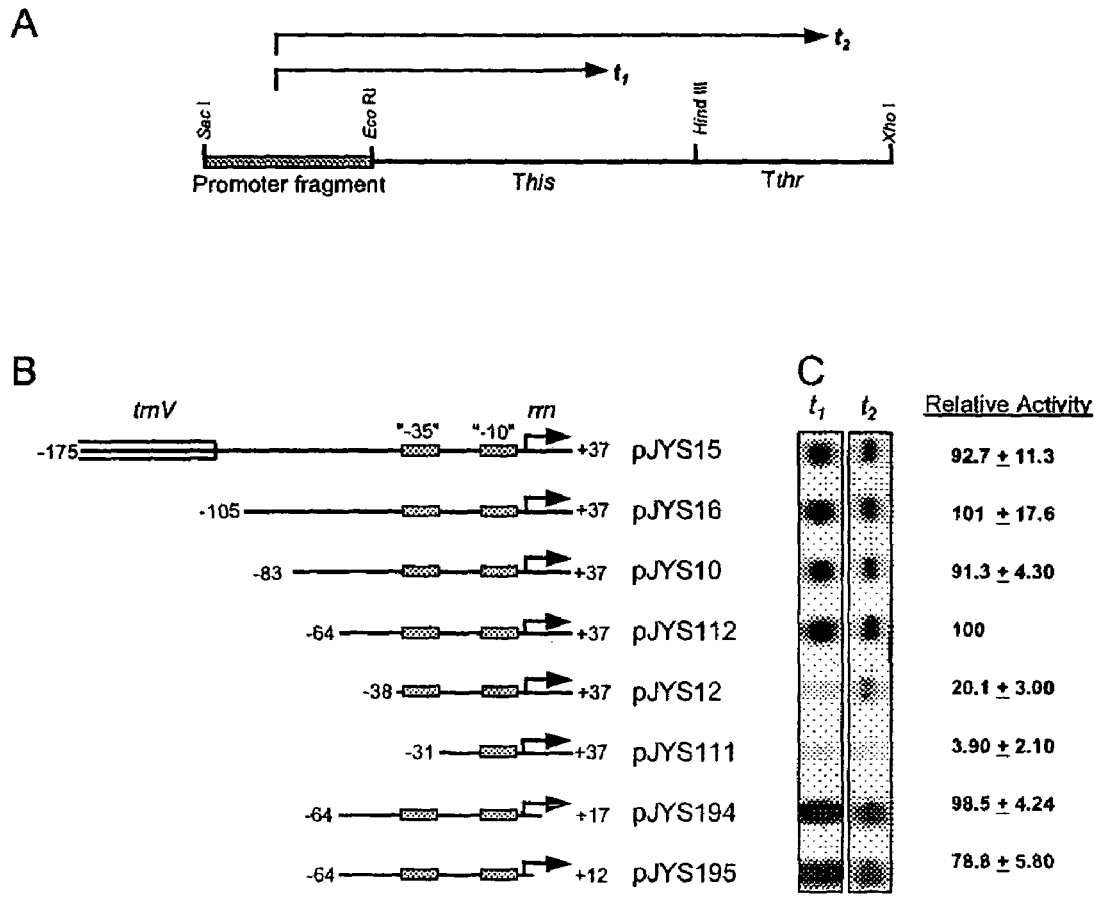
FIGS. 3A, 3B and 3C show the strategy employed for identification of PrrnP1 Upstream Promoter Elements In Vitro.

In vivo promoter analysis is very labor intensive, therefore, we decided to define the PrrnP1 upstream promoter region in vitro. As the first step, we duplicated the in vivo upstream deletion analyses in vitro, and included downstream deletions to define a smaller, fully functional PrrnP1 that is suitable for scanning mutagenesis. Promoter activity was determined by measuring RNA accumulation from mini-genes, which consist of a PrrnP1 promoter derivative and two p-independent bacterial attenuators that function as transcription terminators in vitro (Chen et al., 1990; Liere and Maliga, 1999)(FIG. 3A). In vitro transcription was performed in crude, high salt extracts of purified chloroplasts allowing multi-round transcription during a defined period.

The consequence of deleting sequences upstream of the promoter core was tested on PrrnP1 derivatives with nucleotide +37 at the 3'-end (FIG. 3B). Quantitation of the in vitro transcripts from the PrrnP1 promoter 5' deletion clones is consistent with the in vivo results: sequences between −175 to −83 have no significant effect on promoter activity. The 5'-deletion series included one additional construct not tested in vivo, deletion of sequences between −83 and −64 (pJYS112), which also had no significant affect on'transcription. Deletion of sequences between nucleotides −64 and −38 reduced transcript accumulation by five-fold. Deletion of the conserved −35 promoter element practically abolished in vitro transcription activity (plasmid pJYS111, FIGS. 3B and 3C).

The consequence of deleting sequences downstream of the promoter core was tested on PrrnP1 derivatives with nucleotide −64 at the 5'-end (FIG. 3B). The 3'-end was shortened in two steps, to +17 (pJYS194) and +12 (pJYS195). Data on in vitro transcript accumulation indicate that sequences between −64 and +17 are sufficient for full PrrnP1 promoter activity.

Scanning Mutagenesis to Define PrrnP1 Promoter Architecture In Vitro

Figure 4:
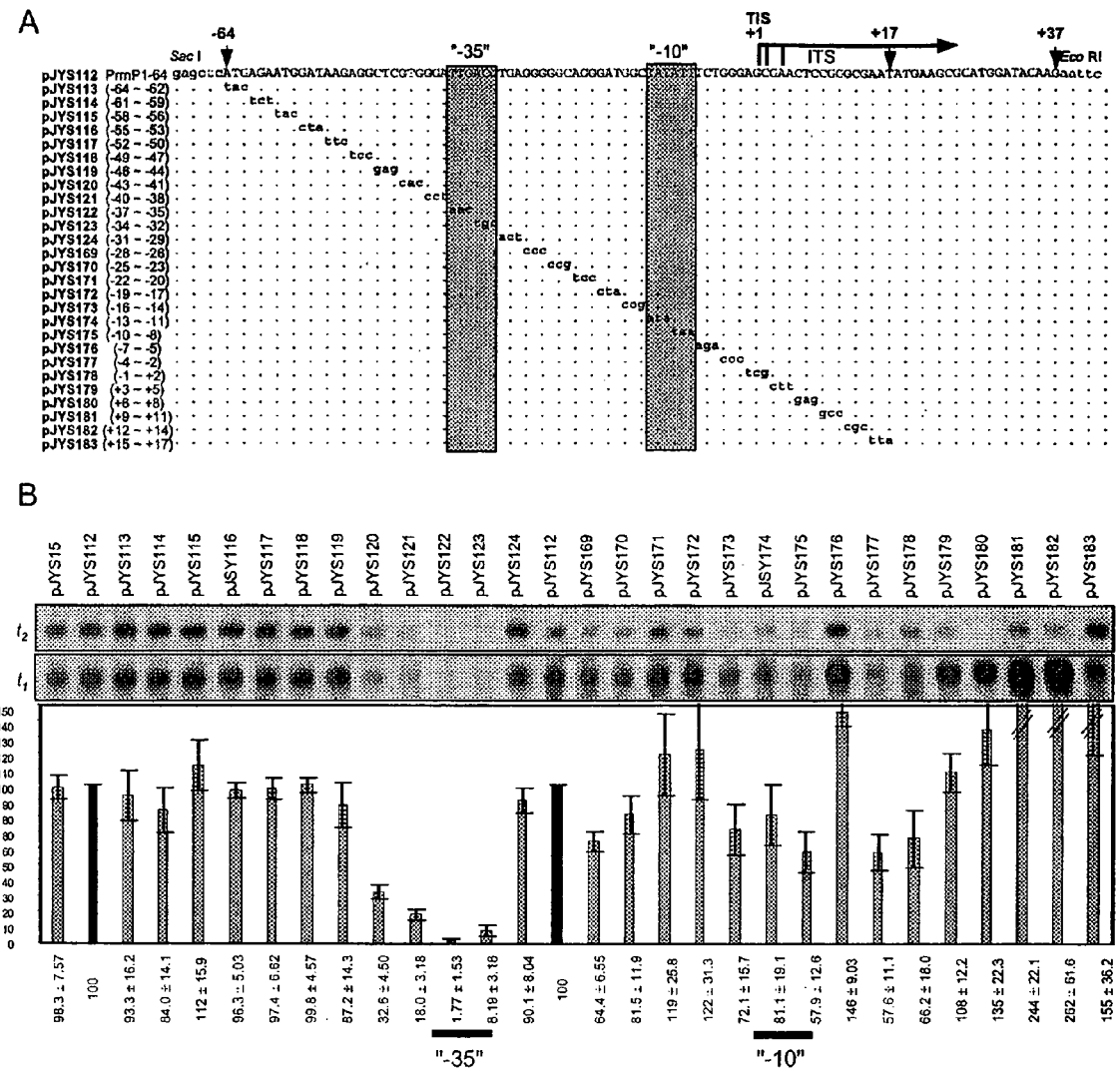
FIGS. 4A and 4B show the results of scanning Mutagenesis for mapping PrrnP1 Promoter Elements In Vitro.

Deletion analysis is suitable to define promoter boundaries. However, individual elements within a promoter can be best defined by systematically changing blocks of sequences within a larger DNA fragment. Therefore, we performed a 3-bp scanning mutagenesis of the full PrrnP1 promoter (−64/+17) defined by deletion analysis in vitro. The point mutations and transcription activity of the promoters are shown in FIG. 4.

In the region upstream of the −35/−10 promoter core mutations significantly (3 to 5 fold) reduced transcription in two clones with mutations in the −43 to −38 region (pJYS120, pJYS121). Point-mutations in the conserved GTGGGA sequence reduced transcription activity to the same extent as deletion of the entire sequence upstream of the conserved −35 promoter element (sequences upstream of −38 position, construct pJYS12, FIG. 3). Since the conserved hexamer is required for PrrnP1 promoter strength, it is designated the plastid rRNA upstream activator (RUA).

Mutagenesis of the core promoter region (nucleotides −37 to −8) significantly affected transcription only in the conserved −35 (TTGACG) promoter element. Mutagenesis of TTG practically abolished (1.77%), whereas mutagenesis of ACG severely reduced (to 8.19%) transcription, confirming the importance of the −35 promoter element in PrrnP1 promoter recognition. However, mutations including the −10 promoter element (−16/−8 region, plasmids pJYS173, pJYS174, pJYS175) only moderately reduced (to 70–80%) in vitro transcription. Mutagenesis of the G-rich sequence (G-patch) between nucleotides −28 to −23 also reduced transcription activity by ~30% (pJYS169, pJYS170) (FIG. 4). Interestingly, mutation in sequences downstream of the transcription initiation site (TIS) from +9 to +14 (pJYS181, pJYS182) caused an increase in transcription activity of at least 2 fold.

To directly address the role the −10 sequence, the first and last T of the hexamer was mutated to A, as these mutations essentially abolished transcription from the psbD, rbcL and psbA promoters (Kim et al., 1999). These mutations reduced PrrnP1 activity only to 46%, confirming a relatively limited role for the −10 region in PrrnP1 recognition by the PEP (FIG. 5).

Ribosomal RNA Upstream Activating Sequence

In this study we have identified a conserved hexameric sequence, GTGGGA (SEQ ID NO: 50), the rRNA operon RUA element directly upstream of the −35 box, as an essential sequence required for overall PrrnP1 promoter activity. Apparently, RUA is the only element upstream of the promoter core. Based on in vivo deletion analysis, sequences upstream of nucleotide −83 do not significantly contribute to promoter function. The in vitro analyses then pinpointed RUA as the source of promoter strength. Thus PrrnP1, as all characterized plastid promoters, is remarkably compact, lacking regulatory sequences far upstream or downstream of the −35/−10 promoter core. The only exception is the blue-light regulated psbD promoter: the AAG box is located between −36 to −64 and the PGT-box is located between −71 to −100, respectively (Allison and Maliga, 1995; Kim and Mullet, 1995; Kim et al., 1999; Thum et al., 2001). The *E. coli* rrnB P1 promoter has two distinct sets of regulatory elements: the UP element (−40 to −60) that is part of the promoter recognition domain and Fis binding sites (−64 to −150). In contrast, the plastid promoter core appears to lack regulatory regions that extend far upstream from the core.

Figure 6:
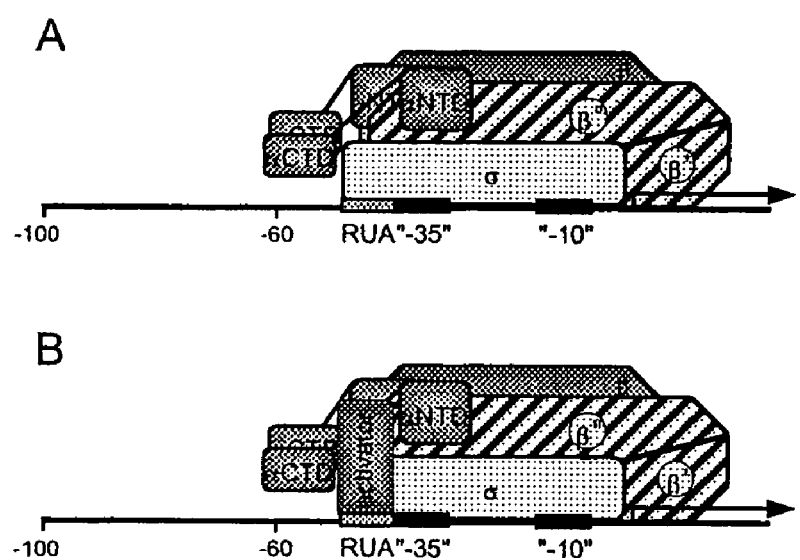
FIG. 6 depicts a model for Interaction of the PEP with the PrrnP1 Promoter.

It is possible that the RUA directly interacts with a component of the PEP itself in which case the RUA acts as an extension of the promoter core facilitating binding of the PEP and enhancing promoter strength. In this case the plastid RUA would play a role similar to the E. coli rrnB P1 UP element which is responsible for increasing promoter strength by direct interaction with RNA polymerase a subunit C-terminal domains (Ross et al., 1993). RUA could be recognized by a plant sigma factor in a manner in which the extended −10 element is recognized by bacterial $\sigma^{70}$ factors (Bown et al., 1997)(FIG. 6A). Various plant sigma factors have been shown to exhibit promoter preference in vitro (Tiller and Link, 1993) (Hakimi et al., 2000) and in vivo (Kanamaru et al., 2001) and exhibit organ-specific, light-induced, circadian and developmentally regulated expression patterns (Isono et al., 1997; Tanaka et al., 1997; Kestermann et al., 1998; Tozawa et al., 1998; Lahiri et al., 1999; Morikawa et al., 1999; Tan and Troxler, 1999; Fujiwara et al., 2000; Lahiri and Allison, 2000; Tsunoyama et al., 2002). Thus, an interaction of the RUA with a specific sigma factor(s) could be the means to selectively regulate transcription of the tobacco rRNA operon. Direct interaction of RUA with the PEP would be a factor-independent mechanism to enhance rrn transcription. The alternative factor-dependent mechanism would involve a nuclear-encoded, plastid-targeted factor that would bind to the RUA and facilitate binding of the PrrnP1 promoter by the PEP (FIG. 6B).

Preliminary analysis of the PrrnP1 promoter has been reported in pea (Sun et al., 1989). Since transcription was carried out with linear DNA, a poor template for the PEP, the pea data are not directly comparable to our results.

The Role of the Conserved −10 Promoter Element in PrrnP1 Function

PrrnP1 contains the conserved −35 (TTGACG) and −10 (TATATT) promoter elements that are a variant of the sigma 70-type consensus sequence (TTGaca and TataaT, respectively) obtained for plastid promoters (Link, 1994). Mutagenesis of either of the conserved promoter elements is expected to abolish promoter activity (Sugiura, 1992; Gruissem and Tonkyn, 1993; Link, 1994, 1996; Liere and Maliga, 2001; Kim, 1999). Transcription from the psbA and psbD promoters, at least in some species and at certain developmental stages, is dependent only on the −10 promoter element. Interaction of the PEP with the −35 element is probably replaced by interaction with the extended −10 sequence (psbA promoter in wheat) (Satoh et al., 1999), the TATA-like sequence between the −35/−10 elements (psbA promoter in mustard)(Eisermann et al., 1990) or factors binding to sequences upstream of a degenerate −35 element (psbD promoter in barley and tobacco)(Allison and Maliga, 1995; Kim and Mullet, 1995; Kim et al., 1999; Thum et al., 2001). To date, PrrnP1 is the first plastid promoter in higher plants in which the −10 sequence seems to play a minor role. Mutagenesis of the −10 sequence, and of the three nucleotides directly upstream, only slightly reduced transcription activity in vitro (by 20% to 40%; pJYS173, pJYS174, pJYS175; FIG. 4). Mutating the first and last T of the −10 hexamer to an A reduced PrrnP1 activity to 46% (FIG. 5). In contrast, the same mutations had a much more dramatic affect on transcription of the strong rbcL, psbD and psbA promoters (Kim et al., 1999). We propose that sigma interaction with the −10 element is largely replaced by direct PEP-RUA (protein-DNA) interaction or by protein-protein interaction between the PEP and the RUA-binding transcription factor (see above).

Initial Transcribed Sequence Affects Transcription Efficiency

Mutations between sequences +9 to +14 (pJYS181, pJYS182) cause a ~2-fold increase in transcription activity (FIG. 4). This region corresponds to the Initial Transcribed Sequence (ITS; +1 to +20) of E. coli promoters. The phenomenon of enhanced transcript accumulation due to mutagenesis of the PrrnP1 +9 to +14 sequences is reminiscent of enhanced transcript accumulation from strong E. coli promoters due to mutagenesis of the ITS region (Chan and Gross, 2001). Strong promoter contacts in E. coli were shown to promote RNA polymerase binding, but impede promoter escape with a concomitant increase in the number of abortive short RNA products that form in the open complex of the RNA polymerase. This abortive initiation phase ends when the RNA polymerase moves away from the promoter and full-size transcripts are formed. Sequences within the ITS region were found to affect the frequency of promoter escape and formation of "productive" transcripts, that explains enhanced transcript accumulation due to mutagenesis of the PrrnP1 ITS region.

G-patches: An Unusual Feature of the PrrnP1 Promoter

Figure 7:
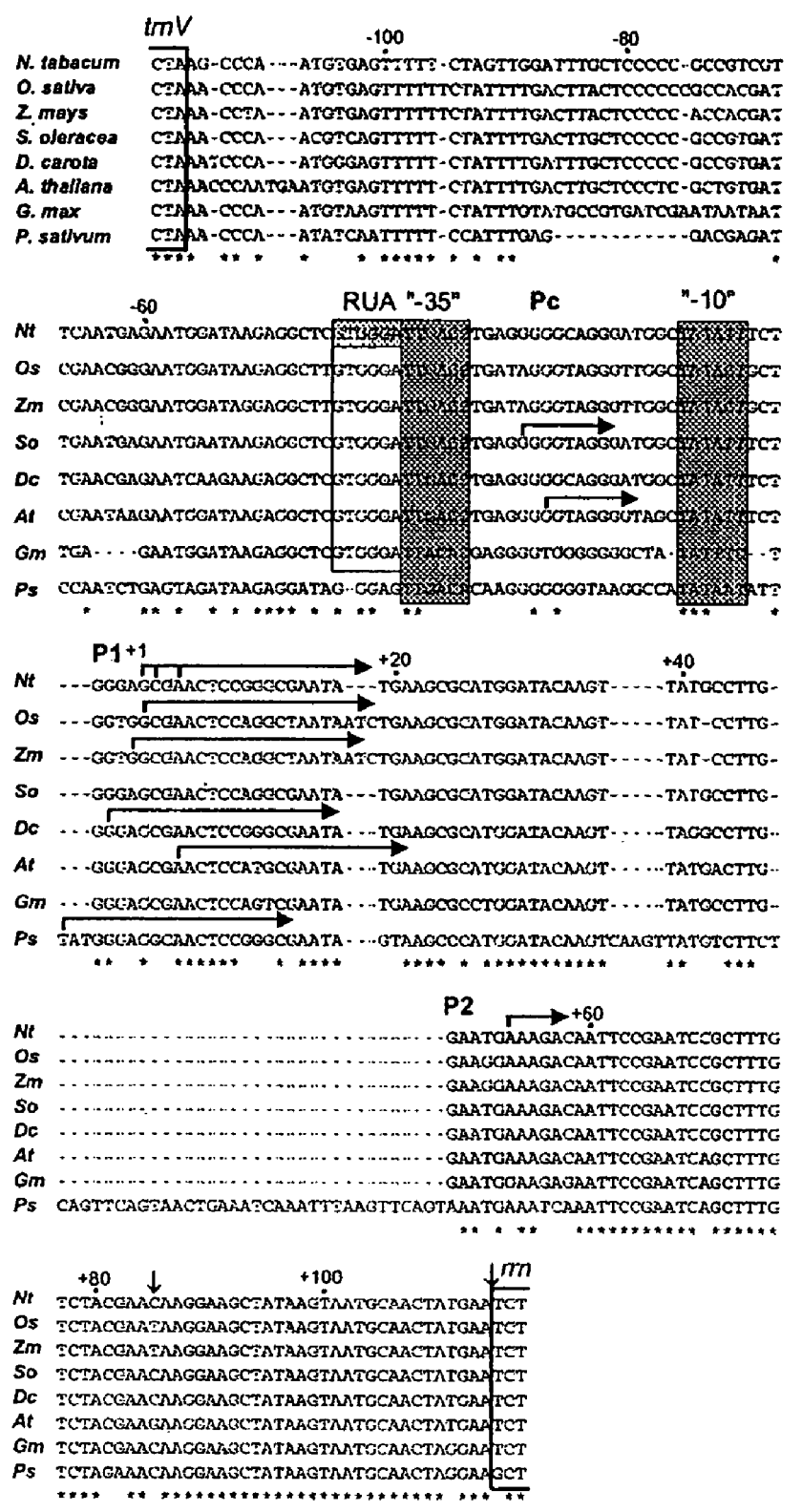

The GC content of the plastid genome is relatively low, 37.85% (GenBank Accession No. Z00044). A striking feature of the tobacco PrrnP1 promoter is the preponderance of conserved G residues between the −35 and −10 promoter elements and in the region downstream of the promoter core (FIG. 7). The cognate regions of the promoters of other highly expressed plastid genes, rbcL, psbA and psbD tend to be AT-rich. Mutagenesis of these G-patches only slightly reduced transcript accumulation in vitro (mutants pJYS169, pJYS170, pJYS177; FIG. 4). However, the G-patches may have a role at specific stages during development similar to the role of TATA-like sequences in psbA transcription (Eisermann et al., 1990).

Conservation of PrrnP1 Promoter Elements

An alignment of the trnv and rRNA operon intergenic region for tobacco, rice, maize, spinach, carrot, *Arabidopsis* and pea is shown in FIG. 7. Position of the conserved RUA, −35 and −10 PrrnP1 promoter elements and transcription initiation sites are marked. The RUA, −35 and −10 promoter elements are conserved in each of the species, except pea, suggesting a shared mechanism for the regulation of rRNA transcription in monocots and dicots. Interestingly, RUA is also present in spinach, a species in which PrrnP1 is not recognized as a promoter (Iratni et al., 1994; Iratni et al., 1997; Bligny et al., 2000). Conservation of a functional PrrnP1 promoter in spinach has been confirmed by showing that it is faithfully recognized by the PEP in tobacco plastids when driving expression of a reporter gene. Therefore, absence of a PrrnP1-specific transcription factor has been proposed as the reason for the lack of transcription from this promoter in spinach (Sriraman et al., 1998a). This explanation is compatible with factor-dependent activation of transcription from the PrrnP1 promoter. The alternative, factor-independent activation mechanism would imply species-specific differences in the PEP subunit interacting with the RUA sequence. Transcription from the PrrnP1 and Pc promoters in *Arabidopsis* chloroplasts is not mutually exclusive as both promoters are simultaneously recognized (Sriraman et al., 1998a). Thus, *Arabidopsis* is different from spinach, in which only Pc is utilized (Iratni et al., 1994; Iratni et al., 1997; Bligny et al., 2000).

Pea is the only species in the alignment in FIG. 7 in which the GTGGGA RUA sequence is poorly conserved: there is insertion of a G between the RUA and −35 element and the first two nucleotides of the hexamer are altered. Thus, pea has the taGGGAg sequence instead of GTGGGA sequence upstream of the −35 element. Nevertheless, transcription of the rRNA operon in pea is from the PrrnP1 promoter (Sun et al., 1989). For comparison, we have included the sequence of another legume, soybean, in which the RUA element is conserved but there are point mutations in both the −35 and −10 promoter elements relative to the other species. Transcript 5'-ends upstream of the soybean rrn operon have not been mapped. Given all the variations from the rrn promoters of other dicot species, it is possible that the legumes have developed yet another unique promoter variant for plastid rrn transcription.

EXAMPLE II

In the previous example, we have demonstrated that a conserved hexameric sequence directly upstream of the −35 hexameric element significantly contributes to PrrnP1 promoter strength. This RUA element may be combined with other plastid core promoters to favorably enhance promoter strength. Since the RUA sequence is present in a large number of species, these chimeric promoters may be utilized to advantage in biotechnological applications. The data reveal additional regions of Prrn that appear to affect promoter function. These are referred to as Prrn transcription modulating elements (PTME) and include the RUA, the −35 hexamer, the G-patch, −10 region, the spacer between the −10 and TIS and the ITS region (FIG. 4). The Prrn promoter is exceptional. For example, the rbcL (Shinozaki and Sugiura, 1982; Shiina et al., 1998) and atpE (Kapoor et al., 1994) promoters comprise −35 and −10 promoter elements only. Addition of one or more of the aforementioned PTME to other core promoters known in the art should beneficially alter promoter strength and developmental timing of plastid gene expression. When combining these PTME with other core promoter sequences, it is desirable to approximate the sequence spacing of the elements observed in the wild type Prrn promoter. This entails aligning the −35 and −10 regions of such promoters and operably linking at least one PTME as desired. Particularly useful for obtaining high levels of transcription is the combination of the RUA, −35 and G-patch of Prrn with the −10 and sequences between the −10 and the transcription initiation site.

Figure 8:
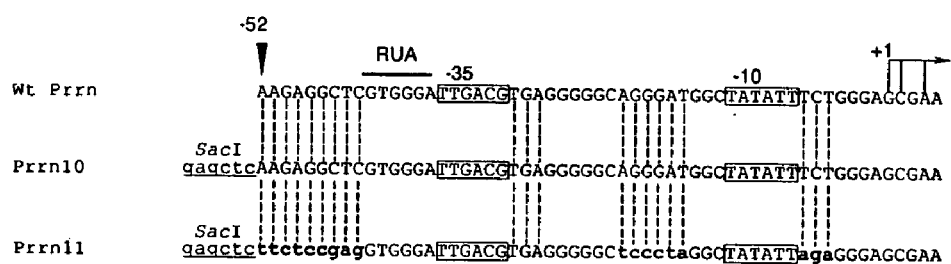
FIG. 8 shows block mutagenesis of nucleotides in the wild-type Prrn promoter (Wt Prrn: nucleotides 18–75 of SEQ ID NO: 3; Prrn10: SEQ ID NO: 52) at neutral positions to minimize DNA sequence homology of Prrn promoters. The mutant derivative is Prrn11 (SEQ ID NO: 51). The sequences shown are suitable for combination with translation control sequences for transgene expression, as described in pending patent application wO 00/07421 for increasing protein expression levels.

The data presented herein provide useful information for the design of improved Prrn promoters, which are less prone to undergo homologous recombination with the plastid genome. The strong Prrn promoter is the preferred choice for the expression of recombinant proteins in chloroplasts (Maliga, 2003). Since the Prrn promoter is naturally present upstream of the plastid rRNA operon, insertion of transgenes with the Prrn promoter duplicates the Prrn promoter region. Loop-out via directly repeated sequences may lead to the loss of transgenes, an approach that is utilized for the selective removal of marker genes from the plastid genome (Iamtham and Day, 2000). The minimal Prrn promoter defined here is smaller than promoter fragments used in earlier work (U.S. Pat. Nos. 5,877,402 and 6,388,168) reducing the opportunity for homologous recombination which is desirable for certain applications. Furthermore, we have determined that mutations at certain nucleotide positions do not affect promoter function. These nucleotides can be combined to further reduce the probability of plastid genome rearrangements by homologous recombination. An example for combining neutral mutations in a Prrn promoter derivative is Prrn11 (SEQ ID NO: 51) shown in FIG. 8.

U.S. Pat. No. 5,877,402 provides a number of plastid promoter sequences which are suitable for combination with the PTME of the present invention. As mentioned previously, translation control sequences which enhance translation of heterologous proteins in higher plants are described in WO/00070421 and are also useful when operably linked to the PTME of the invention. Table 1 below provides a list of promoters suitable for combination with the PTME of the invention.

TABLE 1

| PEP promoters | |
|---|---|
| atpB (−611, 502, 488, −255), atpI (−130) clpP (−95) | U.S. Pat. No. 6,472,586 and cited references |
| psbA, rbcL, psbD | U.S. Pat. No. 5,877,402; Liere and Maliga (2001) ; and references cited |
| rrnB, trnQ, trnH, trnK, trnG, trnS, psbA, rps16, psbK | Link, 1994 |
| atpE | Kapoor et al. 1994 |

REFERENCES

Aiyar, S. E., Gourse, R. L., and Ross, W. (1998). Upstream A-tracts increase bacterial promoter activity through interactions with the RNA polymerase alpha subunit. Proc. Natl. Acad. Sci. USA 95, 14652–14657.

Allison, L. A., and Maliga, P. (1995). Light-responsive and transcription-enhancing elements regulate the plastid psbD core promoter. EMBO J. 14, 3721–3730.

Allison, L. A., Simon, L. D., and Maliga, P. (1996). Deletion of rpoB reveals a second distinct transcription system in plastids of higher plants. EMBO J. 15, 2802–2809.

Baumgartner, B. J., Rapp, J. C., and Mullet, J. E. (1993). Plastid genes encoding the transcription/translation apparatus are differentially transcribed early in barley (*Hordeum vulgare*) chloroplast development: evidence for selective stabilization of psbA mRNA. Plant Physiol. 101, 781–791.

Bligny, M., Courtois, F., Thaminy, S., Chang, C. C., Lagrange, T., Baruah-Wolff, J., Stern, D., and Lerbs-Mache, S. (2000). Regulation of plastid rDNA transcription by interaction of CDF2 with two different RNA polymerases. EMBO J. 19, 1851–1860.

Bown, J., Barne, K., Minchin, S., and Busby, S. (1997). Extended −10 promoters. Nucleic Acids Mol. Biol. 11, 41–52.

Chan, C. L., and Gross, C. A. (2001). The anti-initial transcribed sequence, a portable sequence that impedes promoter escape, requires $S^{70}$ for function. J. Biol. Chem. 276, 38,201–238,209.

Chen, L. J., Rogers, S. A., Bennett, D. C., Hu, M. C., and Orozco, E. M. J. (1990). An in vitro transcription termination system to analyze chloroplast promoters: identification of multiple promoters for the spinach atpB gene. Curr. Genet. 17, 55–64.

Chun, L., Kawakami, A., and Christopher, D. A. (2001). Phytochrome A mediates blue light and UV-A-dependent chloroplast gene transcription in green leaves. Plant Physiol. 125, 1957–1966.

Dempsey, D., Wobbe, K. W., and Klessig, D. (1993). Resistance and susceptible responses of *Arabidopsis thaliana* to turnip crinkle virus. Mol. Plant. Pathol. 83, 1021–1029.

DuBell, A. N., and Mullet, J. E. (1995). Differential transcription of pea chloroplast genes during light-induced leaf development. Plant Physiol. 109, 105–112.

Eisermann, A., Tiller, K., and Link, G. (1990). In vitro transcription and DNA binding characteristics of chloroplast and etioplast extracts from mustard (*Sinapis alba*) indicate differential usage of the psbA promoter. EMBO J. 9, 3981–3987.

Fujiwara, M., Nagashima, A., Kanamaru, K., Tanaka, K., and Takahashi, H. (2000). Three new nuclear genes, sigD, sigE and sigF, encoding putative plastid RNA polymerase sigma factors in *Arabidopsis thaliana*. FEBS Lett. 481, 47–52.

Gourse, R. L., Ross, W., and Gaal, T. (2000). UPs and downs in bacterial transcription initiation: the role of the alpha subunit of RNA polymerase in promoter recognition. Mol. Microbiol. 37, 687–695.

Gruissem, W., and Zurawski, G. (1985). Analysis of promoter regions for the spinach chloroplast rbcL, atpB and psbA genes. EMBO J. 4, 3375–3383.

Gruissem, W., and Tonkyn, J. C. (1993). Control mechanisms of plastid gene expression. Crit. Rev. Plant Sci. 12, 19–55.

Hakimi, M. A., Privat, I., Valay, J. G., and Lerbs-Mache, S. (2000). Evolutionary conservation of C-terminal domains of primary sigma$^{70}$-type transcription factors between plants and bacteria. J. Biol. Chem. 275, 9215–9221.

Hirvonen, C. A., Ross, W., Wozniak, C. E., Marasco, E., Anthony, J. R., Aiyar, S. E., Newburn, V. H., and Gourse, R. L. (2001). Contributions of UP elements and the transcription factor FIS to expression from the seven rrn P1 promoters in *Escherichia coli*. J. Bacteriol. 183, 6305–6314.

Hubschmann, T., and Borner, T. (1998). Characterisation of transcript initiation sites in ribosome-deficient barley plastids. Plant. Mol. Biol. 36, 493–496.

Iratni, R., Baeza, L., Andreeva, A., Mache, R., and Lerbs-Mache, S. (1994). Regulation of rDNA transcripion in chloroplasts: promoter exclusion by constitutive repression. Genes Dev. 8, 2928–2938.

Iratni, R., Diederich, L., Harrak, H., Bligny, M., and Lerbs-Mache, S. (1997). Organ-specific transcription of the rrn operon in spinach plastids. J. Biol. Chem. 272, 13676–13682.

Isono, K., Shimizu, M., Yoshimoto, K., Niwa, Y., Satoh, K., Yokota, A., and Kobayashi, H. (1997). Leaf-specifically expressed genes for polypeptides destined for chloroplasts with domains of sigma70 factors of bacterial RNA polymerases in *Arabidopsis thaliana*. Proc. Natl. Acad. Sci. USA 94, 14948–14953.

Jolly, S. O., and Bogorad, L. (1980). Preferential transcription of cloned maize chloroplast DNA sequences by maize chloroplast RNA polymerase. Proc. Natl. Acad. Sci. USA 77, 822–826.

Kanamaru, K., Nagashima, A., Fujiwara, M., Shimada, H., Shirano, Y., Nakabayashi, K., Shibata, D., Tanaka, K., and Takahashi, H. (2001). An *Arabidopsis* sigma factor (SIG2)-dependent expression of plastid-encoded tRNAs in chloroplasts. Plant. Cell. Physiol. 42, 1034–1043.

Kestermann, M., Neukirchen, S., Kloppstech, K., and Link, G. (1998). Sequence and expression characteristics of a nuclear-encoded chloroplast sigma factor from mustard (*Sinapis alba*). Nucleic Acids. Res. 26, 2747–2753.

Kim, M., and Mullet, J. E. (1995). Identification of a sequence-specific DNA binding factor required for transcription of the barley chloroplast blue light-responsive psbD-psbC promoter. Plant Cell 7, 1445–1457.

Kim, M., Thum, K. E., Morishige, D. T., and Mullet, J. E. (1999). Detailed architecture of the barley chloroplast psbD-psbC blue light-responsive promoter. J. Biol. Chem. 274, 4684–4692.

Lahiri, S. D., and Allison, L. A. (2000). Complementary expression of two plastid-localized sigma-like factors in maize. Plant Physiol. 123, 883–894.

Lahiri, S. D., Yao, J., McCumbers, C., and Allison, L. A. (1999). Tissue-specific and light-dependent expression within a family of nuclear-encoded sigma-like factors from *Zea mays*. Mol. Cell. Biol. Res. Commun. 1, 14–20.

Liere, K., and Maliga, P. (1999). In vitro characterization of the tobacco rpoB promoter reveals a core sequence motif conserved between phage-type plastid and plant mitochondrial promoters. EMBO J. 18, 249–257.

Liere, K., and Maliga, P. (2001). Plastid RNA polymerases in higher plants. In Regulation of Photosynthesis., B. Anderson and E. M. Aro, eds (Dordrecht: Kluwer Academic Publishers), pp. 29–49.

Link, G. (1984). DNA sequence requirements for the accurate transcription of a protein-coding plastid gene in a plastid in vitro transcription system from mustard (*Sinapis alba* L.). EMBO J. 3, 1697–1704.

Link, G. (1994). Plastid differentiation: organelle promoters and transcription factors. In Plant Promoters and Transcription factors—Results & Problems in Cell Differentiation, L. Nover, ed (Berlin: Springer Verlag), pp. 65–85.

Link, G. (1996). Green life: control of chloroplast gene transcription. BioEssays 18, 465–471.

Manna, F., Massardo, D. R., Wolf, K., Luccarini, G., Carlomagno, M. S., Rivellini, F., Alifano, P., and Del-Giudice, L. (1994). A tRNA gene mapping within the chloroplast rDNA cluster is differentially expressed during the development of *Daucus carota*. Nucleic Acids. Res. 22, 1712–1718.

Morikawa, K., Ito, S., Tsunoyama, Y., Nakahira, Y., Shiina, T., and Toyoshima, Y. (1999). Circadian-regulated expression of a nuclear-encoded plastid sigma factor gene (sigA) in wheat seedlings. FEBS Lett. 451, 275–278.

Orozco, E. M., Jr., Mullet, J. E., and Chua, N. H. (1985). An in vitro system for accurate transcription initiation of chloroplast protein genes. Nucleic Acids. Res. 13, 1283–1302.

Orozco, E. M., Jr., Mullet, J. E., Hanley-Bowdoin, L., and Chua, N. H. (1986). In vitro transcription of chloroplast protein genes. Methods Enzymol. 118, 232–253.

Pfannschmidt, T., and Link, G. (1997). The A and B forms of plastid DNA-dependent RNA polymerase from mustard (*Sinapis alba* L.) transcribe the same genes in a different developmental context. Mol. Gen. Genet. 257, 35–44.

Rao, L., Ross, W., Appleman, J. A., Gaal, T., Leirmo, S., Schlax, P. J., Record, M. T., and Gourse, R. L. (1994). Factor independent activation of rrnB P1. An "extended" promoter with an upstream element that dramatically increases promoter strength. J. Mol. Biol. 235, 1421–1435.

Ross, W., Thompson, J. F., Newlands, J. T., and Gourse, R. L. (1990). *E. coli* Fis protein activates ribosomal RNA transcription in vitro and in vivo. EMBO J. 9, 3733–3742.

Ross, W., Gosink, K. K., Salomon, J., Igarashi, K., Zou, C., Ishihama, A., Severinov, K., and Gourse, R. L. (1993). A third recognition element in bacterial promoters: DNA binding by the alpha subunit of RNA polymerase. Science 262, 1407–1413.

Satoh, J., Baba, K., Nakahira, Y., Tsunoyama, Y., Shiina, T., and Toyoshima, Y. (1999). Developmental stage-specific multi-subunit plastid RNA polymerases (PEP) in wheat. Plant J. 18, 407–415.

Shiina, T., Allison, L., and Maliga, P. (1998). rbcL transcript levels in tobacco plastids are independent of light:

reduced dark transcription rate is compensated by increased mRNA stability. Plant Cell 10, 1713–1722.

Silhavy, D., and Maliga, P. (1998). Plastid promoter utilization in a rice embryonic cell culture. Curr. Genet. 34, 67–70.

Sriraman, P., Silhavy, D., and Maliga, P. (1998a). Transcription from heterologous rRNA operon promoters in chloroplasts reveals requirement for specific activating factors. Plant Physiol. 117, 1495–1499.

Sriraman, P., Silhavy, D., and Maliga, P. (1998b). The phage-type PclpP-53 plastid promoter comprises sequences downstream of the transcription initiation site. Nucleic Acids. Res. 26, 4874–4879.

Staub, J. M., and Maliga, P. (1993). Accumulation of D1 polypeptide in tobacco plastids is regulated via the untranslated region of the psbA mRNA. EMBO J. 12, 601–606.

Stiekema, W. J., Heidekamp, F., Dirkse, W. G., van Beckum, J., de Haan, P., ten Bosch, C., and Louwerse, J. D. (1988). Molecular cloning and analysis of four potato tuber mRNAs. Plant. Mol. Biol. 11, 255–269.

Strittmatter, G., Godzicka-Josefiak, A., and Kössel, H. (1985). Identification of an rRNA operon promoter from *Zea mays* chloroplast which excludes the proximal tRNAVal from the primary transcript. EMBO J. 4, 599–604.

Sugiura, M. (1992). The chloroplast genome. Plant. Mol. Biol. 19, 149–168.

Sun, E., Wu, B. W., and Tewari, K. K. (1989). In vitro analysis of the pea chloroplast 16S rRNA gene promoter. Mol. Cell. Biol. 9, 5650–5659.

Svab, Z., and Maliga, P. (1993). High-frequency plastid transformation in tobacco by selection for a chimeric aada gene. Proc. Natl. Acad. Sci. USA 90, 913–917.

Tan, S., and Troxler, R. F. (1999). Characterization of two chloroplast RNA polymerase sigma factors from *Zea mays*: photoregulation and differential expression. Proc. Natl. Acad. Sci. USA 96, 5316–5321.

Tanaka, K., Tozawa, Y., Mochizuki, N., Shinozaki, K., Nagatani, A., Wakasa, K., and Takahashi, H. (1997). Characterization of three cDNA species encoding plastid RNA polymerase sigma factors in *Arabidopsis thaliana*: evidence for the sigma factor heterogeneity in higher plant plastids. FEBS Lett. 413, 309–313.

Thum, K. E., Kim, M., Morishige, D. T., Eibl, C., Koop, H. U., and Mullet, J. E. (2001). Analysis of barley chloroplast psbD light-responsive promoter elements in transplastomic tobacco. Plant. Mol. Biol. 47, 353–366.

Tiller, K., and Link, G. (1993). Sigma-like transcription factors from mustard (*Sinapis alba* L.) etioplast are similar in size to, but functionally distinct from, their chloroplast counterparts. Plant. Mol. Biol. 21, 503–513.

Tozawa, Y., Tanaka, K., Takahashi, H., and Wakasa, K. (1998). Nuclear encoding of a plastid sigma factor in rice and its tissue- and light-dependent expression. Nucleic Acids. Res. 26, 415–419.

Tsunoyama, Y., Morikawa, K., Shiina, T., and Toyoshima, Y. (2002). Blue light specific and differential expression of a plastid sigma factor, Sig5 in *Arabidopsis thaliana*. FEBS Lett. 516, 225–228.

Vera, A., and Sugiura, M. (1995). Chloroplast rRNA transcription from structurally different tandem promoters: an additional novel-type promoter. Curr. Genet. 27, 280–284.

Wakasugi, T., Sugita, M., Tzudzuki, T., and Sugiura, M. (1998). Updated gene map of tobacco chloroplast DNA. Plant Mol. Biol. Reptr. 16, 231–241.

Iamtham, S. and Day, A. (2000) Removal of antibiotic resistance genes from transgenic tobacco plastids. *Nat. Biotechnol.* 18, 1172–1176.

Kapoor, S., Wakasugi, T., Deno, H. and Sugiura, M. (1994) An atpE-specific promoter within the coding region of the atpB gene in tobacco chloroplast DNA. *Curr. Genet.* 26, 263–268.

Maliga, P. (2003) Progress towards commercialization of plastid transformation technology. *Trends Biotech.* 21, 20–28.

Shinozaki, K. and Sugiura, M. (1982) The nucleotide sequence of the tobacco chloroplast gene for the large subunit of ribulose-1,5-bisphosphate carboxylase/oxygenase. *Gene* 20, 91–102.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

---

What is claimed is:

1. An isolated nucleic acid molecule for promoting expression of heterologous molecules in the plastids of higher plants, wherein said nucleic acid molecule comprises SEQ ID NO: 51.

2. A nucleic acid molecule comprising the nucleic acid molecule of claim 1 operably linked to a nucleic acid molecule encoding a heterologous molecule of interest or precursor thereof.

3. A vector comprising the nucleic acid molecule of claim 2.

4. A transgenic plant comprising the vector of claim 3.

\* \* \* \* \*